(12) United States Patent
Katsuki et al.

(10) Patent No.: US 8,367,871 B2
(45) Date of Patent: Feb. 5, 2013

(54) PROCESS FOR PRODUCTION OF OPTICALLY ACTIVE SULFOXIDE COMPOUND USING IRON-SALAN COMPLEX CATALYST

(75) Inventors: Tsutomu Katsuki, Fukuoka (JP); Hiromichi Egami, Fukuoka (JP)

(73) Assignee: Nissan Chemical Industries, Ltd., Tokyo (JP)

( * ) Notice: Subject to any disclaimer, the term of this patent is extended or adjusted under 35 U.S.C. 154(b) by 586 days.

(21) Appl. No.: 12/450,004

(22) PCT Filed: Mar. 10, 2008

(86) PCT No.: PCT/JP2008/054317
§ 371 (c)(1),
(2), (4) Date: Sep. 8, 2009

(87) PCT Pub. No.: WO2008/111563
PCT Pub. Date: Sep. 18, 2008

(65) Prior Publication Data
US 2010/0094037 A1 Apr. 15, 2010

(30) Foreign Application Priority Data
Mar. 9, 2007 (JP) .................................. 2007-061045

(51) Int. Cl.
C07C 315/00 (2006.01)
B01J 23/00 (2006.01)
(52) U.S. Cl. ............... 568/27; 568/28; 568/34; 502/325
(58) Field of Classification Search .................... None
See application file for complete search history.

(56) References Cited

U.S. PATENT DOCUMENTS
(Continued)

FOREIGN PATENT DOCUMENTS
JP  A-7-82195   3/1995
JP  A-10-072430 3/1998
(Continued)

OTHER PUBLICATIONS

Sivasubramanian, V. et al., "Iron(III)-salen complexes as enzyme models. Mechanistic study of oxo(salen)iron complexes oxygenation of organic sulfides," J.Org.Chem. (2002) 67: 1506-1514.*

(Continued)

*Primary Examiner* — Karl J Puttlitz
(74) *Attorney, Agent, or Firm* — Oliff & Berridge, PLC

(57) ABSTRACT

An optically active sulfoxide compound that is useful as an intermediate for synthesis or an active ingredient of a physiologically active substance such as a pharmaceutical agent is produced at a high optical purity. A process for producing an optically active sulfoxide compound of formula (4) comprises oxidizing a sulfide compound of formula (3) in the presence of an optically active metal complex of formula (1), (1'), (2) or (2') by using an oxidizing agent. The present invention is also directed to the optically active metal complex.

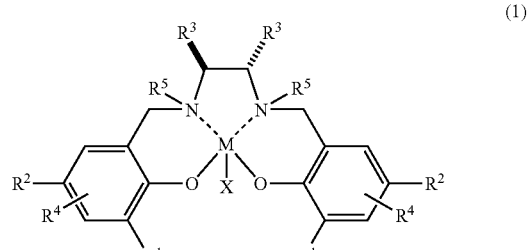

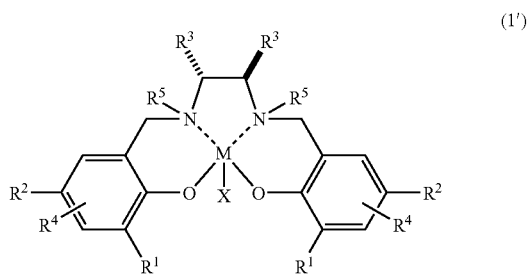

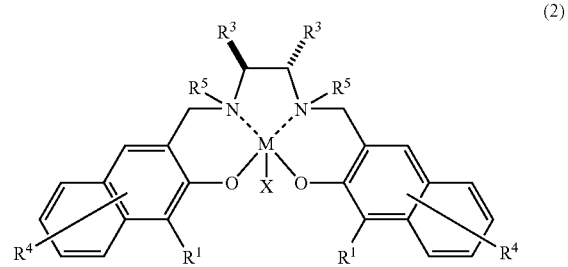

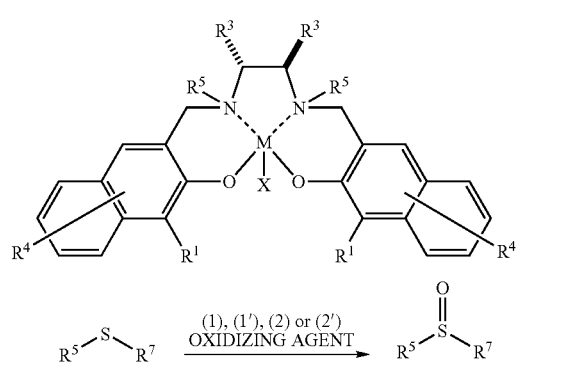

9 Claims, No Drawings

U.S. PATENT DOCUMENTS

| | | | |
|---|---|---|---|
| 6,521,561 B1* | 2/2003 | Jacobsen et al. | 502/162 |
| 2008/0071099 A1* | 3/2008 | Katsuki et al. | 549/523 |
| 2008/0234502 A1* | 9/2008 | Kondo et al. | 549/396 |

FOREIGN PATENT DOCUMENTS

| | | |
|---|---|---|
| JP | A-2002-308845 | 10/2002 |
| JP | A-2004-323445 | 11/2004 |
| WO | WO 2006/087874 AI | 8/2006 |

OTHER PUBLICATIONS

Yeori, A. et al. "Diastereoisomerically selective enantiomerically pure titanium complexes of salan ligands: synthesis, structure and preliminary activity studies," Inorg. Chem. (2005) 44: 4466-8.*

Venkataramanan, N. et al. "Metal-salen complexes as efficient catalysts for the oxygenation of heteroatom containing organic compounds—synthetic and mechanistic aspects," Coord. Chem. Rev. (2005) 249: 1249-68.*

Sawada, Y. et al. "Titanium-salan-catalyzed asymmetric epoxidation with aqueous hydrogen peroxide as the oxidant," Angew. Che. Int. Ed. (2006) 45: 3478-80.*

Pitchen et al., "An Efficient Asymmetric Oxidation of Sulfides to Sulfoxides," J. Am. Chem. Soc., vol. 106, No. 26, pp. 8188-8193, American Chemical Society, 1984.

Brunel et al., "Highly Enantioselective Oxidation of Sulfides Mediated by a Chiral Titanium Complex," J. Org. Chem., vol. 60, No. 24, pp. 8086-8088, 1995.

Komatsu et al., "Catalytic Asymmetric Oxidation of Sulfides to Sulfoxides Using R-(+)-Binaphthol," Tetrahedron Letters, vol. 33, No. 37, pp. 5391-5394, Pergamon Press Ltd, Great Britain, 1992.

Komatsu et al., "Catalytic Asymmetric Oxidation of Sulfides to Sulfoxides with tert-Butyl Hydroperoxide Using Binaphthol as a Chiral Auxiliary," J. Org. Chem. vol. 58, No. 17, pp. 4529-4533, American Chemical Society, 1993.

Ando et al., "Oxiation of Sulfide with ArIO Catalyzed with TPPM(III)C1," Tetrahedron Letters, vol. 23, No. 16, pp. 1685-1688, Pergamon Press Ltd, Great Britain, 1982.

Groves et al., "Asymmetric Hydroxylation, Epoxidation, and Sulfoxidation Catalyzed by Vaulted Binaphthyl Metalloporphyrins," J. Org. Chem., vol. 55, No. 11, pp. 3628-3634, American Chemical Society, 1990.

Nakajima et al., "Asymmetric Oxidation of Sulfides to Sulfoxides by Organic Hydroperoxides with Optically Active Schiff Base-Oxovanadium(IV) Catalysts," Chemistry Letters, pp. 1483-1486, The Chemical Society of Japan, 1986.

Palucki et al, "Asymmetric Oxidation of Sulfides with $H_2O_2$ Catalyzed by (salen)Mn(III) Complexes," Tetrahedron Letters, vol. 33, No. 47, pp. 7111-7114, Pergamon Press Ltd, Great Britain, 1992.

Noda et al., "Asymmetric Oxidation of Sulfides Using (Salen)manganese(III) Complex as a Catalyst," Tetrahedron Letters, vol. 35, No. 12, pp. 1887-1890, 1994.

Ohta et al., "Vanadium-catalyzed Enantioselective Sulfoxidation of Methyl Aryl Sulfides with Hydrogen Peroxide as Terminal Oxidant," No. 1, pp. 161-163, Thieme Stuttgart, New York, 2002.

Pelotier et al., "Enantioselective Sulfide Oxidation with $H_2O_2$: A Solid Phase and Array Approach for the Optimisation of Chiral Schiff Base-Vanadium Catalysts," No. 7, pp. 1055-1060, Thieme Stuttgart, New York, 2002.

Weix et al., "Improved Synthesis of tert-Butanesulfinamide Suitable for Large-Scale Production," Organic Letters, vol. 5, No. 8, pp. 1317-1320, American Chemical Society, 2003.

Sun et al., "Efficient Asymmetric Oxidation of Sulfides and Kinetic Resolution of Sulfoxides Catalyzed by a Vanadium-Salan System," J. Org. Chem., vol. 69, No. 24, pp. 8500-8503, 2004.

Drago et al., "Vanadium-Catalyzed Sulfur Oxidation/Kinetic Resolution in the Synthesis of Enantiomerically Pure Alkyl Aryl Sulfoxides," Angew. Chem. Int. Ed., vol. 44, pp. 7221-7223, Wiley-VCH Verlag GmbH & Co. KGaA, Weinheim, 2005.

Legros et al., "Iron-Catalyzed Asymmetric Sulfide Oxidation with Aqueous Hydrogen Peroxide," Angew. Chem. Int. Ed., vol. 42, pp. 5487-5489, Wiley-VCH Verlag GmbH & Co. KGaA, Weinheim, 2003.

Legros et al., "Highly Enantioselective Iron-Catalyzed Sulfide Oxidation with Aqueous Hydrogen Peroxide under Simple Reaction Conditions," Angew. Chem. Int. Ed., vol. 43, pp. 4225-4228, Wiley-VCH Verlag GmbH & Co. KGaA, Weinheim, 2004.

Thakur et al., "$WO_3$-30% $H_2O_2$-cinchona alkaloids: a new heterogeneous catalytic system for the asymeetric oxidation of sulfides and the kinetic resolution of racemic sulfoxides," Tetrahedron: Asymmetry, vol. 14, pp. 407-410, Elsevier Science Ltd., 2003.

Pitchen, "The Asymmetric Synthesis of a Biologically Active Sulphoxide," Chemical Industry, No. 16, pp. 636-639, Aug. 15, 1994.

Posner, "Asymmetric Synthesis of Carbon-Carbon Bonds Using Sulfinyl Cycloalkenones, Alkenolides, and Pyrones," Accounts of Chemical Research, vol. 20, No. 2, pp. 72-78, American Chemical Society, Feb. 1987.

Legros et al., "Investigations on the Iron-Catalyzed Asymmetric Sulfide Oxidation," Chemistry A European Journal, vol. 11, No. 4, pp. 1086-1092, Wiley-VCH Verlag GmbH & Co. KGaA, Weinheim, Feb. 4, 2005.

Velusamy et al., "Copper catalyzed oxidation of sulfides to sulfoxides with aqueous hydrogen peroxide," Tetrahedron Letters, vol. 46, No. 22, pp. 3819-3822, Elsevier Ltd., 2005.

International Search Report issued on May 27, 2008 in International Application No. PCT/JP2008/054317.

* cited by examiner

PROCESS FOR PRODUCTION OF OPTICALLY ACTIVE SULFOXIDE COMPOUND USING IRON-SALAN COMPLEX CATALYST

TECHNICAL FIELD

The present invention relates to a process for producing an optically active sulfoxide compound characterized by including asymmetric oxidation of a sulfide compound in the presence of an optically active iron-salan complex catalyst.

BACKGROUND ART

An optically active sulfoxide compound is an important intermediate as an asymmetric aid in asymmetric synthesis.

The optically active sulfoxide compound is used as an asymmetric aid in synthesis of an optically active allyl alcohol derivative (see Patent Document 1, for example). The optically active sulfoxide compound is used as an asymmetric aid also in synthesis of various optically active compounds (see Non-patent Documents 1 and 2, for example).

A large number of pharmaceutical agents containing optically active sulfoxide compound sites have been developed, which indicates that a technique of asymmetric oxidation of sulfide compounds into optically active sulfoxide compounds is useful as a process for producing pharmaceutical agents.

As a method for producing an optically active sulfoxide compound from a sulfide compound, a reaction using titanium-tartaric acid ester as a catalyst (see Non-patent Documents 3 and 4, for example), a reaction using titanium-optically active binaphthol as a catalyst (see Non-patent Documents 5 and 6, for example), a reaction using a metalloporphyrin complex as a catalyst (see Non-patent Documents 7 and 8, for example), a reaction using a metallosalen complex as a catalyst (see Non-patent Documents 9, 10, and 11, for example), and the like are known.

In recent years, a method in which a hydrogen peroxide solution is used as an oxidizing agent has been investigated actively. For example, a reaction using a vanadium complex as a catalyst (see Non-patent Documents 12, 13, 14, 15, and 16, for example), a reaction using an iron complex as a catalyst (see Non-patent Documents 17, 18, and 19, for example), and a reaction using a tungsten complex as a catalyst (see Non-patent Document 20, for example), all of which uses hydrogen peroxide as an oxidizing agent, are known.

[Patent Document 1]
  Japanese Patent Application Publication No. JP-A-7-82195
[Non-patent Document 1]
  Chem. Ind. 15, 636 (1994)
[Non-patent Document 2]
  Acc. Chem. Res. 20, 72 (1987)
[Non-patent Document 3]
  J. Am. Chem. Soc. 106, 8188 (1984)
[Non-patent Document 4]
  J. Org. Chem. 60, 8086 (1995)
[Non-patent Document 5]
  Tetrahedron Lett. 33, 5391 (1992)
[Non-patent Document 6]
  J. Org. Chem. 58, 4529 (1993)
[Non-patent Document 7]
  Tetrahedron Lett. 23, 1685 (1982)
[Non-patent Document 8]
  J. Org. Chem. 55, 3628 (1990)
[Non-patent Document 9]
  Chem. Lett. 1483 (1986)
[Non-patent Document 10]
  Tetrahedron Lett. 33, 7111 (1992)
[Non-patent Document 11]
  Tetrahedron Lett. 35, 1887 (1994)
[Non-patent Document 12]
  Synlett, 1055-1060 (2002)
[Non-patent Document 13]
  Synlett, 161-163 (2002)
[Non-patent Document 14]
  Org. Lett. 5, 1317-1320 (2003)
[Non-patent Document 15]
  J. Org. Chem. 69, 8500-8503 (2004)
[Non-patent Document 16]
  Angew. Chem. Int, Ed., 44, 7221-7223 (2005)
[Non-patent Document 17]
  Angew. Chem. Int, Ed., 42, 5487-5489 (2003)
[Non-patent Document 18]
  Angew. Chem. Int, Ed., 43, 4225-4228 (2004)
[Non-patent Document 19]
  Chem. Eur. J., 11, 1086-1092 (2005)
[Non-patent Document 20]
  Tetrahedron Asymmetry, 14, 407-410 (2003)

DISCLOSURE OF THE INVENTION

Problem to be Solved by the Invention

All of the above methods are reactions using an optically active metal complex as a catalyst, and are very efficient methods. Particularly, the reaction using a hydrogen peroxide solution as an oxidizing agent is excellent in handleability and safeness and is also excellent in terms of atom economy.

However, an organic solvent is essential for all of the above asymmetric reactions using hydrogen peroxide, and moreover, methylene chloride and chloroform with high environmental burden are used in many cases.

Means for Solving the Problem

The present inventors have carried out intensive studies on an asymmetric sulfide oxidation reaction. As a result, they completed the present invention by finding an optically active iron-salan complex as a novel metal complex, and further finding that using the complex as a catalyst provides a high-yield and a highly stereoselective asymmetric oxidation reaction of sulfide with water, but not an organic solvent, as a solvent.

That is, the present invention provides:

1. A process for producing an optically active sulfoxide compound characterized by including:
   carrying out asymmetric oxidation, using an oxidizing agent, of a sulfide compound expressed by Formula (3):

(3)

[where, $R^6$ and $R^7$ are different from each other and each of $R^6$ and $R^7$ is a $C_{6-12}$ aryl group, a $C_{6-12}$ arylmethyl group (the $C_{6-12}$ aryl group and the $C_{6-12}$ arylmethyl group are not substituted or substituted with a halogen atom, a $C_{1-4}$ alkyl group, a $C_{1-4}$ alkoxy group, a $C_{2-5}$ alkylcarbonyloxy group, a $C_{2-5}$ alkoxylcarbonyl group, a nitro group, or a cyano group), or a $C_{1-6}$ alkyl group (the $C_{1-6}$ alkyl group is not substituted or substituted with a halogen atom, a nitro group, a hydroxyl group, or a cyano group), or when $R^6$ is a $C_{6-12}$ aryl group in which the ortho-position of the $C_{6-12}$ aryl group is substituted with a $C_{1-4}$ alkyl group or a $C_{1-4}$ alkoxy group, $R^7$ may be a $C_{2-4}$ bivalent group that forms a fused ring together with a sulfur atom binding to $R^6$];
in the presence of an optically active metal complex expressed by Formula (1), Formula (1'), Formula (2), or Formula (2'):

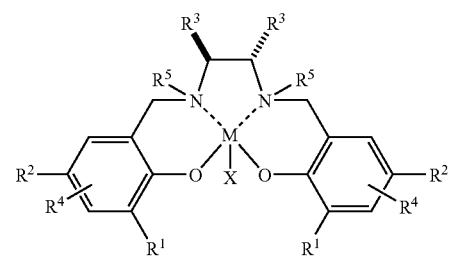
(1)

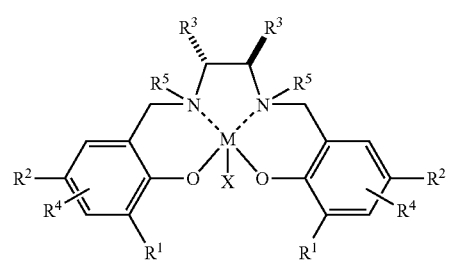
(1')

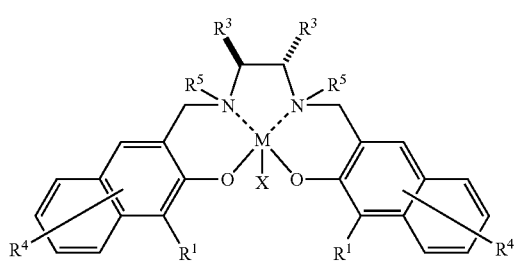
(2)

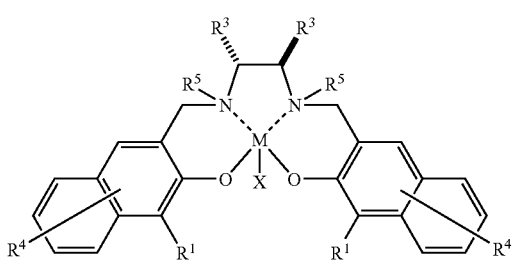
(2')

{in Formula (1), Formula (1'), Formula (2), and Formula (2'),
$R^1$ is a hydrogen atom, a halogen atom, a $C_{1-4}$ alkyl group, a $C_{1-4}$ alkoxy group, a $C_{6-12}$ aryloxy group, or a $C_{6-22}$ aryl group [the aryl group is not substituted or substituted with a $C_{1-4}$ alkyl group (the alkyl group is not substituted or arbitrarily substituted with a halogen atom) or a $C_{1-4}$ alkoxy group (the alkoxy group is not substituted or substituted with a $C_{6-12}$ aryl group), and when the $C_{6-22}$ aryl group forms an axial asymmetry with an aromatic ring in Formula (2) and Formula (2'), the axial asymmetry may be either optically active or optically inactive],
$R^2$ is a hydrogen atom, a halogen atom, a $C_{1-4}$ alkyl group, a $C_{1-4}$ alkoxy group, a $C_{6-12}$ aryloxy group, or a $C_{6-12}$ aryl group, $R^3$ is a $C_{1-4}$ alkyl group, a $C_{6-18}$ aryl group, or a $C_{3-5}$ bivalent group in which two $R^3$s together form a ring,
$R^4$ is a hydrogen atom, a halogen atom, a $C_{1-4}$ alkyl group, a $C_{1-4}$ alkoxy group, a nitro group, or a cyano group independently,
$R^5$ is a hydrogen atom or a $C_1$ alkyl group,
M is an iron atom, and
X means an anion that can form an ion pair with M}; in which
the optically active sulfoxide compound is expressed by Formula (4):

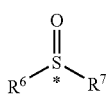
(4)

(where, $R^6$ and $R^7$ have the same meaning as defined in Formula (3) and an absolute configuration of a sulfur atom indicated with an asterisk (*) is R or S).
2.
A process for producing an optically active sulfoxide compound characterized by including:
converting, by selective oxidation using an oxidizing agent, a racemate or one of optical isomers of a sulfoxide compound with low optical purity expressed by Formula (5):

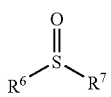
(5)

(where, $R^6$ and $R^7$ have the same meaning as defined in Formula (3)),
into a sulfone compound expressed by Formula (6):

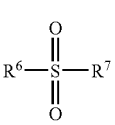
(6)

(where, $R^6$ and $R^7$ have the same meaning as defined in Formula (5)), in the presence of the optically active metal complex expressed by Formula (1), Formula (1'), Formula (2), or Formula (2') as described in 1. to kinetically obtain an optically active sulfoxide compound expressed by Formula (4):

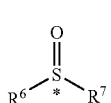
(4)

(where, $R^6$ and $R^7$ have the same meaning as defined in Formula (6) and an absolute configuration of a sulfur atom indicated as an asterisk (*) is R or S).
3.
The process for producing an optically active sulfoxide compound according to 1. or 2., in which when $R^6$ is a $C_{6-12}$ aryl group or a $C_{6-12}$ arylmethyl group (the $C_{6-12}$ aryl group and the $C_{6-12}$ arylmethyl group are not substituted or substituted with a halogen atom, a $C_{1-4}$ alkyl group, a $C_{1-4}$ alkoxy group, a $C_{2-5}$ alkylcarbonyloxy group, a $C_{2-5}$ alkoxycarbonyl group, a nitro group, or a cyano group) and $R^7$ is a $C_{1-4}$ alkyl group or when $R^6$ is a $C_{6-12}$ aryl group in which the ortho-position of the $C_{6-12}$ aryl group is substituted with a $C_{1-4}$ alkyl group or a $C_{1-4}$ alkoxy group, $R^7$ is a $C_{2-4}$ bivalent group that forms a fused ring together with a sulfur atom binding to $R^6$.

4.

The process for producing an optically active sulfoxide compound according to any one of 1. to 3., in which hydrogen peroxide is used as an oxidizing agent.

5.

The process for producing an optically active sulfoxide compound according to any one of 1. to 4., characterized in that a reaction is carried out in the presence of an optically active metal complex, in Formula (2) or Formula (2'), $R^1$ is a $C_{6-22}$ aryl group [the aryl group is not substituted or substituted with a $C_{1-4}$ alkyl group (the alkyl group is not substituted or arbitrarily substituted with a halogen atom) or a $C_{1-4}$ alkoxy group (the alkoxy group is not substituted or substituted with a $C_{6-12}$ aryl group), and when the $C_{6-22}$ aryl group forms an axial asymmetry with an aromatic ring in Formula (2) or Formula (2'), the axial asymmetry may be optically active or optically inactive], $R^2$ is a hydrogen atom, $R^3$ is a tetramethylene group in which two $R^3$s together form a ring, $R^4$ is a hydrogen atom, $R^5$ is a hydrogen atom or a methyl group, and X is a chlorine atom.

6.

The process for producing an optically active sulfoxide compound according to 5., in which the reaction is carried out in the presence of the optically active metal complex in which $R^1$ is an aryl group forming an axial asymmetry with an aromatic ring in Formula (2) or Formula (2') and the axial asymmetry is optically active.

7.

The process for producing an optically active sulfoxide compound according to 6., in which the reaction is carried out in the presence of the optically active metal complex in which $R^1$ is a 1-phenyl naphthyl group.

The present invention also provides:

8.

An optically active metal complex or an enantiomer thereof expressed by Formula (7):

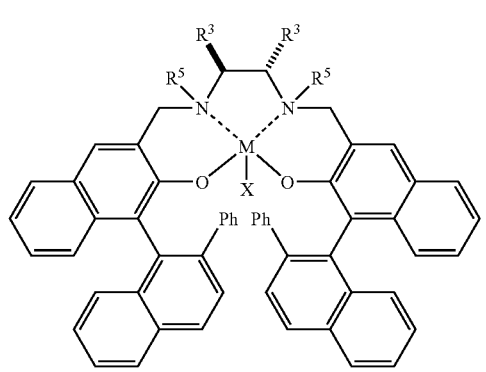

(7)

(in Formula (7), $R^3$ is a $C_{1-4}$ alkyl group, a $C_{6-18}$ aryl group, or a $C_{3-5}$ bivalent group in which two $R^3$s together form a ring, $R^5$ is a hydrogen atom or a $C_{1-4}$ alkyl group, M is an iron atom, and X means an anion that can form an ion pair with M), in which a binaphthyl skeleton is optically active or optically inactive.

Effects of the Invention

According to the methods of the present invention, an optically active sulfoxide compound expressed by Formula (4) can be produced, using a water solvent, but not an organic solvent, by oxidizing a sulfide compound expressed by Formula (3) in the presence of an optically active iron complex expressed by Formula (1), Formula (1'), Formula (2), or Formula (2') using an oxidizing agent.

According to the present invention, a reaction, in which either of optical isomers of a sulfoxide compound expressed by Formula (5) is converted into a sulfone compound expressed by Formula (6) by selective oxidation using an oxidizing agent in the presence of an optically active metal complex expressed by Formula (1), Formula (1'), Formula (2), or Formula (2'), and in which therefore an optically active sulfoxide compound expressed by Formula (4) is kinetically obtained, is also efficiently carried out using water, but not an organic solvent, as a solvent.

BEST MODES FOR CARRYING OUT THE INVENTION

One aspect of the present invention relates to a process for producing an optically active sulfoxide compound expressed by Formula (4) by asymmetric oxidation of a sulfide compound expressed by Formula (3) using an oxidizing agent in the presence of an optically active metal complex expressed by Formula (1), (1'), (2), or (2'). Predominancy of generation of either an R form or an S form of the optically active sulfoxide compound expressed by Formula (4) during the asymmetric oxidation varies depending on reaction conditions such as a structure of a reactive substrate, a structure of an optically active metal complex used for a reaction, or a type of a solvent.

Another aspect of the present invention relates to a process for producing an optically active sulfoxide compound expressed by Formula (4) by selective oxidation of a racemate or either one of optical isomers of a sulfoxide compound with low optical purity expressed by Formula (5) using an oxidizing agent in the presence of an optically active metal complex expressed by Formula (1), (1'), (2), or (2') into a sulfone compound. Which of an R form or an S form of a sulfoxide compound is selectively oxidized during its oxidation into a sulfone compound depends on reaction conditions such as a structure of a reactive substrate, a structure of an optically active metal complex used for a reaction, or a type of a solvent. Therefore, the production process of this aspect is to obtain the optically active sulfoxide compound expressed by (4) by converting either one of optical isomers of a sulfoxide compound as a raw material by the above selective oxidation into a sulfone compound expressed by Formula (6) and therefore kinetically, or as a result, by changing the purity of the optically active sulfoxide compound as a raw material so that a desired optically active substance is increased.

The present invention will be described in further detail. In the present invention, "n" means normal, "i" means iso, "s" or "sec" means secondary, "t" or "tert" means tertiary, "c" means cyclo, "o" means ortho, "m" means meta, "p" means para, and "Ph" means phenyl.

First, $R^1$, $R^2$, $R^3$, $R^4$, $R^5$, $R^6$, $R^7$, and X are described.

Examples of a $C_{1-4}$ alkyl group in the present invention include a methyl group, an ethyl group, a n-propyl group, an i-propyl group, a n-butyl group, an i-butyl group, a sec-butyl group, and a tert-butyl group; preferably a methyl group and an ethyl group.

Examples of a $C_{1-6}$ alkyl group include a methyl group, an ethyl group, a n-propyl group, a c-propyl group, an i-propyl group, a c-propyl group, a n-butyl group, an i-butyl group, a sec-butyl group, a tert-butyl group, a n-pentyl group, an i-pentyl group, a n-hexyl group, and a c-hexyl group; preferably a methyl group and an ethyl group are preferable.

Examples of a $C_{1-4}$ alkoxyl group include a methoxy group, an ethoxy group, a n-propoxy group, an i-propoxy group, a n-butoxy group, an i-butoxy group, a sec-butoxy group, and a tert-butoxy group; preferably a methoxy group and an ethoxy group.

Examples of a $C_{2-5}$ alkylcarbonyloxy group include a methylcarbonyloxy group, an ethylcarbonyloxy group, a n-propylcarbonyloxy group, an i-propylcarbonyloxy group, a n-butylcarbonyloxy group, an i-butylcarbonyloxy group, a sec-butylcarbonyloxy group, a tert-butylcarbonyloxy group, a n-amylcarbonyloxy group, an i-amylcarbonyloxy group, and a neopentylcarbonyloxy group; preferably a methylcarbonyloxy group and an ethylcarbonyloxy group.

Examples of a $C_{2-5}$ alkoxycarbonyl group include a methoxycarbonyl group, an ethoxycarbonyl group, a n-propoxycarbonyl group, an i-propoxycarbonyl group, a n-butoxycarbonyl group, an i-butoxycarbonyl group, a sec-butoxycarbonyl group, a tert-butoxycarbonyl group, a n-amyloxycarbonyl group, an i-amyloxycarbonyl group, and a neopentyloxycarbonyl group; preferably a methoxycarbonyl group and an ethoxycarbonyl group.

A $C_{6-12}$ aryloxy group is an oxy group substituted with aromatic hydrocarbon having 6 to 12 carbon atoms, and examples thereof include a phenyloxy group, a 2-methylphehyloxy group, a 1-naphthyloxy group, a 2-naphthyloxy group, a 2-biphenyloxy group; and preferably a phenyloxy group and a 1-naphthyloxy group.

A $C_{6-22}$ aryl group is an aromatic hydrocarbon having 6 to 22 carbon atoms, and preferably, examples thereof include a phenyl group, a 2-methylphenyl group, a 2-ethylphenyl group, a 1-naphthyl group, a 2-naphthyl group, a 2-biphenylyl group, a 2-phenyl-1-naphthyl group, a 2-(m-biphenylyl)-1-naphthyl group, and a 2-(p-biphenyl)-1)-1-naphthyl group (an axial asymmetry in the 2-phenyl-1-naphthyl group, the 2-(m-biphenylyl)-1-naphthyl, or the 2-(p-biphenylyl)-1-naphthyl group is optically active or optically inactive); more preferably, a phenyl group, a 2-methylphenyl group, and a 2-phenyl-1-naphthyl group.

A $C_{6-18}$ aryl group is an aromatic hydrocarbon having 6 to 18 carbon atoms, and preferably, examples thereof include a phenyl group, a 2-methylphenyl group, a 3,5-dimethylphenyl group, a 2,4,6-trimethylphenyl group, and a 1-naphthyl group, a 2-naphthyl group; more preferably, a phenyl group, a 3,5-dimethylphenyl group, and a 2,4,6-trimethylphenyl group.

A $C_{6-12}$ aryl group is an aromatic hydrocarbon having 6 to 12 carbon atoms, and examples thereof include a phenyl group, a 2-methylphenyl group, a 1-naphthyl group, a 2-naphthyl group, and a 2-biphenylyl group; preferably a phenyl group and a 2-naphthyl group.

A $C_{6-12}$ arylmethyl group is a methyl group substituted with aromatic hydrocarbon having 6 to 12 carbon atoms, and examples thereof include a benzyl group, a 1'-methylphenylmethyl group, a 1'-naphthylmethyl group, a 2'-naphthylmethyl group, and a 2'-biphenylmethyl group; preferably a benzyl group and a 1'-naphthylmethyl group.

A halogen atom represents a fluorine atom, a chlorine atom, a bromine atom, and an iodine atom.

Examples of a $C_{3-5}$ bivalent group in which two $R^3$s together form a ring include a trimethylene group, a tetramethylene group, and a pentamethylene group; preferably a tetramethylene group and a pentamethylene group, and more preferably a tetramethylene group.

Examples of a $C_{2-4}$ bivalent group in which $R^7$ forms a fused ring together with a sulfur atom binding to $R^6$ when $R^6$ is a $C_{6-12}$ aryl group in which the ortho-position of the $C_{6-12}$ aryl group is substituted with a $C_{1-4}$ alkyl group or a $C_{1-4}$ alkoxy group, include a dimethylene group, a dimethyleneoxy group, a trimethylene group, a trimethyleneoxy group, a tetramethylene group, and a tetramethyleneoxy group; preferably a dimethylene group, a dimethyleneoxy group, and a trimethylene group.

Anions that can form salts of X include, such as, $OH^-$, $F^-$, $Cl^-$, $Br^-$, $I^-$, $CH_3CO_2^-$; $PF_6^-$, $ClO_4^-$, $BF_4^-$, $CO_3^{2-}$, $SO_4^{2-}$, and $PO_4^{3-}$.

Next, an asymmetric sulfide oxidation reaction is described.

Among the sulfide compound expressed by Formula (3), especially preferable sulfide compounds with a combination of substituents $R^6$ and $R^7$ include methyl phenyl sulfide, ethyl phenyl sulfide, methyl o-tolyl sulfide, methyl p-tolyl sulfide, methyl o-nitrophenyl sulfide, methyl p-nitrophenyl sulfide, methyl o-chlorphenyl sulfide, methyl p-chlorphenyl sulfide, methyl o-bromophenyl sulfide, methyl p-bromophenyl sulfide, methyl o-methoxyphenyl sulfide, methyl p-methoxyphenyl sulfide, ethyl o-nitrophenyl sulfide, methyl 1-naphthyl sulfide, methyl 2-naphthyl sulfide, methyl 2-pyridyl sulfide, methyl benzyl sulfide, and ethyl benzyl sulfide.

Examples of an oxidizing agent includes iodosylbenzene, iodosylmesitylene, iodosobenzoic acid, sodium hypochloride, calcium hypochloride, and hydrogen peroxide; preferably hydrogen peroxide.

An amount of used oxidizing agent may be in a range of 1- to 20-fold moles; preferably 1- to 10-fold moles, relative to the sulfide compound of Formula (1).

Among optically active iron complexes expressed by Formula (1), Formula (1'), Formula (2), and Formula (2'), examples of an especially preferable structure of catalysts with a combination of substituents include the following optically active iron complexes and enantiomers thereof.

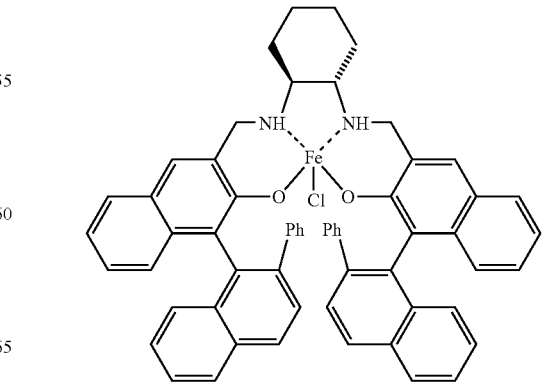

-continued

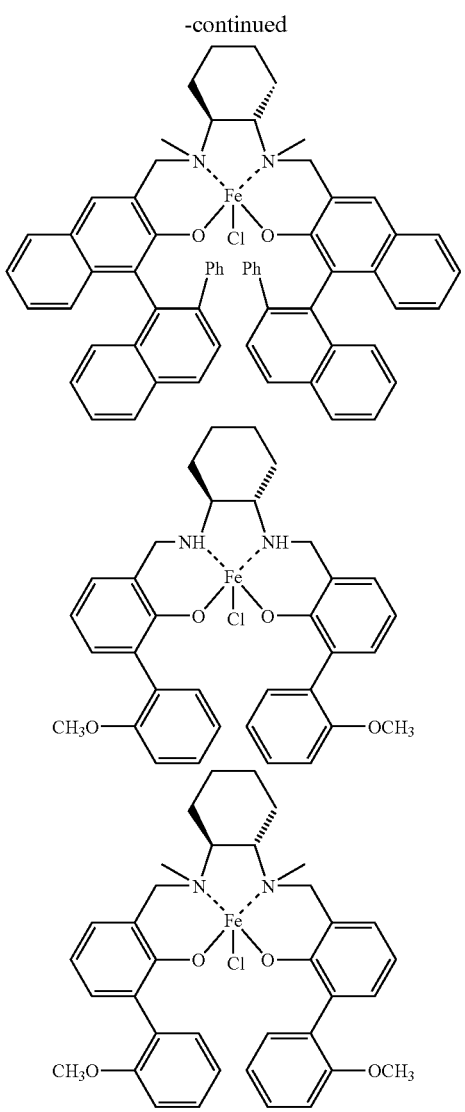

The amount of used optically active metal complex may be in a range of 0.01 to 50 mol %, preferably 0.1 to 10 mol %, relative to the sulfide compound of Formula (3).

Reaction solvents are not particularly limited as long as the reaction solvents are not involved in a reaction, and examples thereof include: water, nitriles such as acetonitrile, propionitrile, and butyronitrile; ketones such as acetone, methyl ethyl ketone, and methylisobutylketone; aromatic hydrocarbons such as benzene, toluene, xylene, mesitylene, chlorobenzene, fluorobenzene, and o-dichlorobenzene; aliphatic hydrocarbons such as n-hexane, cyclohexane, n-octane, and n-decane; esters such as methyl acetate, ethyl acetate, and butyl acetate; halogenated hydrocarbons such as dichloromethane, dichloroethane, and carbon tetrachloride; ethers such as tetrahydrofuran (THF) diethylether, t-butylmethylether, and dimethoxyethane; and alcohols such as methanol, ethanol, 1-propanol, 2-propanol, 1-butanol, 2-butanol, isobutanol, and cyclohexanol; preferably water.

When a reaction is carried out using water as a solvent, an inorganic salt or an organic salt may be dissolved in water. In addition, these reaction solvents can be used singly or in combination with each other.

Examples of a method for adding the oxidizing agent include en bloc addition, divided addition, and serial addition. Divided addition is a method in which the used oxidizing agent is added over a plurality of times. Either equal division or unequal division may be performed, and the time of division is preferably within a range of 2 to 100 times.

The oxidizing agent may be charged as a solid or after dissolved in a solvent. Hydrogen peroxide used as an oxidizing agent is desirably charged as an aqueous solution. The concentration of the solution can be selected as necessary, but it is preferably 0.1 to 70% by mass, more preferably 3 to 60% by mass, and further preferably 10 to 40% by mass.

A reaction temperature is normally within a range of −50° C. to 60° C., preferably −20° C. to 40° C. for a solvent other than a water solvent, and especially 0° C. to 40° C. for water as solvent.

Although it depends on a type of the sulfide compound of Formula (3) to be used, the optically active metal complexes expressed by Formulae (1), (1'), (2), and (2') and an oxidizing agent, a reaction time is normally 0.1 to 1000 hours, more generally 0.1 to 96 hours.

After the completion of the reaction, a desired optically active sulfoxide compound can be isolated by a well known method. Examples of a method for isolation include a method for obtaining the optically active sulfoxide compound of Formula (4) by a operation such as chromatography with using a silica gel, distillation, or crystallization, after extracting a desired substance from a reacted mixture after the reaction using an appropriate solvent and vacuum concentrating a solvent.

The optical purity of the obtained desired substance can be measured by optically active chromatography or optical rotation analysis.

Using a similar metal complex or a reaction system, a racemic sulfoxide compound can be selectively oxidized into a sulfone compound. That is, optically active sulfoxide can be obtained by dynamic kinetic resolution.

EXAMPLES

The present invention will be described in further detail using the following examples; however, the present invention is not limited thereto.

Example 1

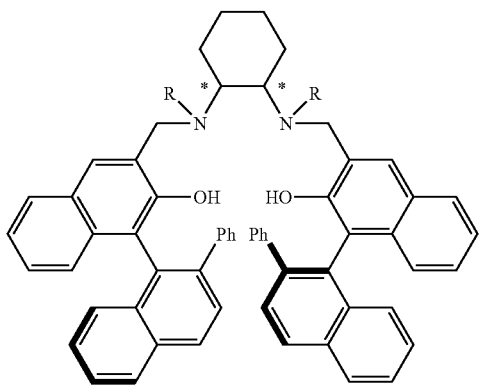

(5): (R, R), R = H
(6): (R, R), R = $CH_3$
(7): (S, S), R = H
(8): (S, S), R = $CH_3$

Synthesis of Salan Ligand (5)

Potassium carbonate (138 mg, 1 mmol) was added to a tetrahydrofuran/methanol (30 mL/6 mL) solution of (R,R)-1,2-cyclohexanediamine sulfate (212 mg, 1 mmol) and (aR)-3-formyl-2-hydroxy-2'-phenyl-1,1'-binaphthyl (748 mg, 2 mmol) synthesized by a method described in Tetrahedron, 50, 11827-11838 (1994). After 10-hour stirring, sodium boron hydride (76 mg, 2 mmol) was added. After further 5-hour stirring, quenching wad performed using an ammonium chloride aqueous solution, and extraction was performed using ethyl acetate. An organic phase was dried over anhydrous sodium sulfate, followed by filtration through Celite. Filtrate was concentrated under reduced pressure and purified by chromatography with a silica gel column (n-hexane/ethyl acetate=1/1) to obtain a salan ligand (5) quantitatively.

IR (KBr): 3053, 2928, 2855, 1626, 1597, 1499, 1437, 1354, 1252, 1113, 822, 760, 700 cm$^{-1}$;

$^1$H NMR: δ 7.98 (d, 2H, J=8.3 Hz), 7.90 (d, 2H, J=8.3 Hz), 7.68-7.58 (m, 4H), 7.41-6.94 (m, 24H), 4.00 (ABq, 4H, J=14.3 Hz), 2.34-2.23 (m, 2H), 1.93-1.80 (m, 2H), 1.60-1.48 (m, 2H), 1.19-1.05 (m, 2H), 0.96-0.82 (m, 2H);

$^{13}$C NMR: δ 153.2, 142.1, 140.0, 134.1, 132.9, 132.8, 131.4, 128.7, 127.9, 127.8, 123.6, 127.3, 127.0, 126.4, 126.3, 126.0, 125.8, 125.5, 125.1, 124.8, 122.7, 119.3, 59.9, 50.5, 30.5, 24.1;

TOFMS (time-of-flight mass spectrometry): ($C_{60}H_{50}N_2O_2+H^+$) Calculated value: m/z=831.3945. Measured value: m/z=831.3950.

Example 2

Synthesis of Salan Ligand (6)

To an acetonitrile (5 mL) solution of the salan ligand (5) (210 mg, 0.25 mmol), a 37% formaldehyde aqueous solution (0.2 mL, 2.46 mmol) and acetic acid (0.6 mL) were added at room temperature. After stirring the mixture for 20 minutes, sodium boron hydride (47 mg, 1.24 mmol) was added. After the mixture was further stirred for 12 hours, acetonitrile was distilled out under reduced pressure, and then 2M sodium hydroxide aqueous solution (0.5 mL) was added to the resulting residue. Extraction was performed using ethyl acetate, and an organic phase was dried over anhydrous sodium sulfate. After filtration, the solution was concentrated under reduced pressure, followed by purification using silica gel column chromatography (n-hexane/ethyl acetate=5/1) to obtain a salan ligand (6) (151 mg, 69%).

IR (KBr): 3053, 2930, 2856, 1626, 1593, 1501, 1464, 1435, 1346, 1250, 1026, 941, 820, 754, 700 cm$^{-1}$;

$^1$H NMR: δ 7.88 (d, 4H, J=8.3 Hz), 7.61-7.50 (m, 4H), 7.44-736 (m, 4H), 7.33-7.00 (m, 12H), 6.93 (d, 2H, J=8.3 Hz), 6.75-6.67 (m, 2H), 6.63-6.55 (m, 4H), 3.93 (ABq, 4H, J=13.4 Hz), 2.76-2.66 (m, 2H), 2.02-1.94 (m, 2H), 1.92 (s, 6H), 1.84-1.73 (m, 2H), 1.31-1.03 (m, 4H);

$^{13}$C NMR: δ 153.6, 140.5, 134.2, 133.0, 132.7, 131.8, 128.4, 128.3, 127.8, 127.6, 127.4, 127.3, 126.8, 126.6, 125.8, 125.7, 125.1, 124.8, 123.8, 122.4, 118.9, 62.2, 59.4, 34.4, 25.6;

TOFMS. ($C_{62}H_{54}N_2O_2+H^+$) Calculated value: m/z=859.4258. Measured value: m/z=859.4258.

Example 3

Synthesis of Salan Ligand (7)

Using (S,S)-1,2-cyclohexanediamine sulfate (212 mg, 1 mmol) and (aR)-3-formyl-2-hydroxy-2'-phenyl-1,1'-binaphthyl (748 mg, 2 mmol), a salan ligand (7) was obtained by a method similar to the method for synthesizing the salan ligand (5).

IR (KBr): 3314, 3051, 2932, 2855, 1626, 1597, 1495, 1429, 1354, 1252, 1113, 822, 764, 748, 700 cm$^{-1}$;

$^1$H NMR: δ 7.96 (d, 2H, J=8.5 Hz), 7.88 (d, 2H, J=8.3 Hz), 7.70 (d, 2H, J=7.8 Hz), 7.62 (d, 2H, J=8.5 Hz), 7.48 (s, 2H), 7.39-7.32 (m, 2H), 7.28-6.95 (m, 2OH), 4.10 (ABq, 4H, J=14.0 Hz), 2.13-2.00 (m, 2H), 1.74-1.53 (m, 4H), 1.00-0.67 (m, 4H);

$^{13}$C NMR: δ 153.3, 142.5, 139.2, 134.6, 133.0, 132.8, 131.4, 128.8, 128.1, 127.9, 127.7, 127.4, 127.3, 127.2, 127.1, 126.6, 126.2, 126.1, 126.0, 125.4, 124.9, 124.5, 122.6, 118.8, 58.0, 48.9, 29.6, 24.5;

TOFMS. ($C_{60}H_{50}N_2O_2+H^+$) Calculated value: m/z=831.3945. Measured value: m/z=831.3945.

Example 4

Synthesis of Salan Ligand (8)

To a tetrahydrofuran (30 mL) solution of salan ligand (7) (831 mg, 1.0 mmol), 60% oily sodium hydride (88 mg, 2.2 mmol) was added at 0° C., followed by 1-hour stirring. Methyl iodide (190 μL, 3.1 mmol) was added, followed by 1-hour stirring. An ammonium chloride aqueous solution was added for quenching, and extraction was performed using ethyl acetate. An organic phase was dried over anhydrous sodium sulfate, followed by filtration through Celite. Filtrate was concentrated under reduced pressure to obtain a mono-N-methylated product.

This product was dissolved in acetonitrile, followed by adding a 37% formaldehyde aqueous solution (0.8 mL, 10 mmol) and acetic acid (2.5 mL). After 20-minute stirring, sodium boron hydride (170 mg, 4.5 mmol) was added, and after 12-hour stirring, acetonitrile was distilled out under reduced pressure, followed by adding a 2M sodium hydroxide aqueous solution. Extraction was carried out using ethyl acetate, and an organic phase was dried over anhydrous sodium sulfate. After filtration, the solution was concentrated under reduced pressure, followed by purification using a silica gel column chromatography (n-hexane/ethyl acetate=5/1) to obtain a salan ligand (8) (784 mg, 91%).

IR (KBr): 3053, 2930, 2855, 1624, 1597, 1497, 1435, 1340, 1250, 1028, 941, 819, 760, 746, 700 cm$^{-1}$;

$^1$H NMR: δ 7.95-7.87 (m, 4H), 7.59 (d, 2H, J=8.5 Hz), 7.49 (d, 2H, J=7.8 Hz), 7.39-6.85 (m, 24H), 3.91 (ABq, 4H, J=13.2 Hz), 2.74-2.62 (m, 2H), 2.05 (s, 6H), 2.01-1.65 (m, 4H), 1.33-0.98 (m, 4H);

$^{13}$C NMR: δ 153.2, 142.1, 139.8, 133.9, 133.0, 132.7, 131.7, 128.7, 128.2, 128.1, 127.7, 127.6, 127.5, 127.3, 126.9, 126.6, 126.0, 12.9, 125.6, 125.4, 124.7, 124.2, 122.4, 118.8, 62.7, 58.0, 35.0, 25.4;

TOFMS. ($C_{62}H_{54}N_2O_2+H^+$) Calculated value: m/z=859.4258. Measured value: m/z=859.4230.

Example 5

Preparation Method of Complex

To ethanol (30 mL) solution of ligand (5), (6), (7) or (8) (0.2 mmol each), iron dichloride (0.2 mmol) was added at room temperature, followed by 1.5-hour stirring and then the mixture was concentrated under reduced pressure. About 200 mg of the concentrate was purified by flash chromatography with a diameter and a length of 3 cm and 5 cm, respectively (silica gel: methylene chloride/methanol=19/1) to obtain a corresponding complex (1), (2), (3), or (4).

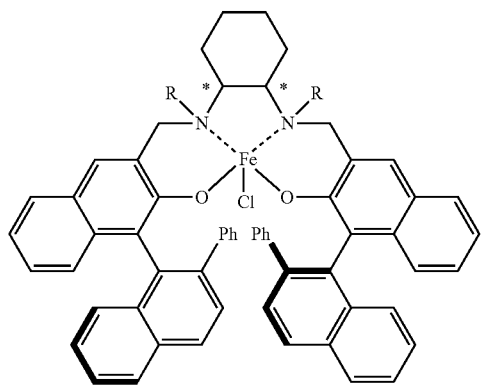

(1): (R, R), R = H
(2): (R, R), R = CH$_3$
(3): (S, S), R = H
(4): (S, S), R = CH$_3$

Complex (1)
Purple Solid;
IR (KBr): 3260, 3053, 2936, 2860, 1620, 1595, 1495, 1421, 1356, 1265, 1207, 1144, 1115, 1028, 951, 823, 752, 702 cm$^{-1}$;
TOFMS. (M$^+$-Cl) Calculated value: m/z=884.3061. Measured value: m/z=884.3074.
Complex (2)
Purple Solid;
IR (KBr): 3051, 2930, 2856, 1622, 1593, 1495, 1431, 1352, 1254, 1146, 1111, 1026, 941, 819, 748, 700 cm$^{-1}$;
TOFMS. (M$^+$-Cl) Calculated value: m/z=912.3374. Measured value: m/z=912.3327.
Complex (3)
Purple Solid;
IR (KBr): 3234, 3049, 2936, 2858, 1618, 1593, 1493, 1450, 1418, 1352, 1259, 1113, 951, 885, 820, 746, 700 cm$^{-1}$;
TOFMS. (M$^+$-Cl) Calculated value: m/z=884.3061. Measured value: m/z=884.3057.
Complex (4)
Purple Solid;
IR (KBr): 3051, 2932, 2858, 1618, 1593, 1495, 1450, 1420, 1354, 1263, 1113, 951, 820, 746, 700 cm$^{-1}$;
TOFMS. (M$^+$-Cl) Calculated value: m/z=912.3374. Measured value: m/z=912.3334.

Example 6

Asymmetric Oxidation of Sulfide Using Iron-Salan Complex Catalyst

A complex (4) (1.9 mg, 1 mol %) was weighed out in a Schlenk flask, to which sulfide (0.2 mmol) was added. Water (0.5 mL) was added to the resultant mixture, followed by stirring it for 10 minutes at 20° C. A 30% hydrogen peroxide solution (33 μL, 1.5 eq) was added to the resultant mixture, followed by stirring it for 3 hours at room temperature. To the reaction mixture, 5 mL of water was added, followed by extraction using ethyl acetate. An organic phase was dried over anhydrous sodium sulfate, followed by filtration and then it was concentrated under reduced pressure. Corresponding sulfoxide was obtained by purifying the concentrate by silica gel column chromatography (ethyl acetate).

Optical purity was determined by HPLC analysis.

Similarly, experiments described in Tables 1 and 2 were carried out. The results are shown in the following tables:
(Table 1)

TABLE 1

Asymmetric oxidation of thioanisole using iron-salan complex

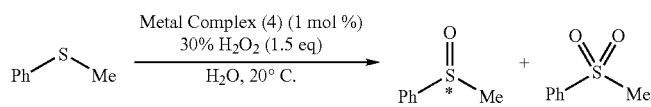 [SMILES: CSc1ccccc1 ; CS(=O)c1ccccc1 ; CS(=O)(=O)c1ccccc1]

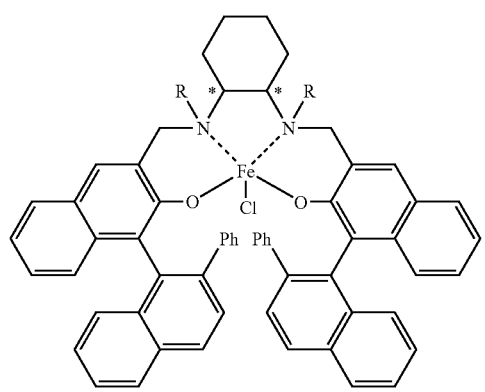

(1): (R,R), R = H
(2): (R,R), R = CH$_3$
(3): (S,S), R = H
(4): (S,S), R =CH$_3$

TABLE 1-continued

| Experiment Number | Metal Complex | Duration (h) | Yield (%)[a] Sulfoxide | Yield (%)[a] Sulfone | Optical Purity e.e.[b,c] |
|---|---|---|---|---|---|
| 1 | (3) (2 mol %) | 3 | 89 | 5 | 88 (S) |
| 2 | (4) (2 mol %) | 3 | 91 | 9 | 96 (S) |
| 3 | (3) (2 mol %) | 0.5 | 73 | <2 | 86 (S) |
| 4 | (4) (2 mol %) | 0.5 | 47 | 1 | 95 (S) |
| 5 | (3) (1 mol %) | 3 | 86 | 4 | 84 (S) |
| 6 | (4) (1 mol %) | 3 | 92 | 8 | 96 (S) |

[a]Yield was determined by $^1$H NMR (400 MHz) analysis.
[b]Optical purity e.e. was determined by HPLC (DAICEL CHIRALCEL OB-H) analysis.
[c]Absolute configuration was determined by comparing the order of elution resulted from HPLC analysis with known samples.

(Table 2)

TABLE 2

Asymmetric oxidation of various sulfide compounds $$Ar\text{-}S\text{-}R \xrightarrow[H_2O,\ 20°C,\ 3h]{\text{Metal Complex (4) (1 mol \%)},\ 30\%\ H_2O_2\ (1.5\ eq)} Ar\text{-}S(O)\text{-}R\ (\text{Sulfoxide}) + Ar\text{-}S(O)_2\text{-}R\ (\text{Sulfone})$$

| Experiment Number | Ar | R | Yield (%)[a] Sulfoxide | Yield (%)[a] Sulfone | Optical Purity e.e.[d] |
|---|---|---|---|---|---|
| 1 | p-CH$_3$C$_6$H$_4$— | CH$_3$ | 91 | 9 | 96[b] |
| 2 | p-CH$_3$OC$_6$H$_4$— | CH$_3$ | 92 | 8 | 95[b] |
| 3 | p-ClC$_6$H$_4$— | CH$_3$ | 76 | 24 | 94[b] |
| 4 | o-ClC$_6$H$_4$— | CH$_3$ | 97 | <1 | 96[b] |
| 5 | o-CH$_3$OC$_6$H$_4$— | CH$_3$ | 99 | <1 | 95[b] |
| 6 | C$_6$H$_5$CH$_2$— | CH$_3$ | 93 | 7 | 87[b] |
| 7 | C$_6$H$_5$— | C$_2$H$_5$ | 78 | 22 | 81[c] |

[a]Yield was determined by $^1$H NMR (400 MHz) analysis.
[b]Optical purity e.e. was determined by HPLC (DAICEL CHIRALCEL OB-H) analysis.

c Optical purity e. e. was determined by HPLC (DAICEL CHIRALCEL OD-H) analysis.
d Absolute configuration was determined by comparing the order of elution resulted from HPLC analysis with known samples.

(S)-phenylmethylsulfoxide

Colorless oily substance; 96% ee; DAICEL CHIRALCEL OB-H, hexane/isopropanol=80/20, flow rate=0.8 mL min$^{-1}$, $t_S$=13.9 min, $t_R$=25.0 min;
$^1$H NMR: δ 7.69-7.63 (m, 2H), 7.57-7.48 (m, 3H), 2.73 (s, 3H).

(S)-p-trimethylsulfoxide

Experiment Number 1

Colorless solid; 96% ee; DAICEL CHIRALCEL OB-H, hexane/isopropanol=50/50, flow rate=0.5 mL min$^{-1}$, $t_S$=10.2 min, $t_R$=16.9 min;
$^1$H NMR: δ 7.55 (d, 2H, J=8.0 Hz), 7.34 (d, 2H, J=8.0 Hz), 2.73 (s, 3H), 2.42 (s, 3H).

(S)-p-methoxyphenylmethylsulfoxide

Experiment Number 2

Colorless oily substance; 95% ee; DAICEL CHIRALCEL OB-H, hexane/isopropanol=50/50, flow rate=0.5 mL min$^{-1}$, $t_S$=13.5 min, $t_R$=23.2 min;
$^1$H NMR: δ 7.63-7.56 (m, 2H), 7.07-7.00 (m, 2H), 3.86 (s, 3H), 2.70 (s, 3H).

(S)-p-chlorophenylmethylsulfoxide

Experiment Number 3

Colorless oily substance; 94% ee; DAICEL CHIRALCEL OB-H, hexane/isopropanol=80/20, flow rate=0.5 mL min$^{-1}$, $t_S$=18.1 min, $t_R$=27.8 min;
$^1$H NMR: δ 7.64-7.57 (m, 2H), 7.55-7.49 (m, 2H), 2.73 (s, 1H).

(S)-o-chlorophenylmethylsulfoxide

Experiment Number 4

Colorless oily substance; 96% ee; DAICEL CHIRALCEL OB-H, hexane/isopropanol=80/20, flow rate=0.5 mL min$^{-1}$, $t_S$=16.6 min, $t_R$=29.1 min;
$^1$H NMR: δ 7.96 (dd, 1H, J=1.2, 7.8 Hz), 7.55 (t, 1H, J=7.3 Hz), 7.51-7.36 (m, 2H), 2.84 (s, 3H).

(S)-o-methoxyphenylmethylsulfoxide

Experiment Number 5

Colorless oily substance; 95% ee; DAICEL CHIRALCEL OB-H, hexane/isopropanol=80/20, flow rate=0.5 mL min$^{-1}$, $t_S$=18.2 min, $t_R$=36.3 min;
$^1$H NMR: δ 7.83 (dd, 1H, J=1.7, 7.8 Hz), 7.49-7.42 (m, 1H), 7.23-7.16 (m, 1H), 6.93 (d, 1H, J=8.1 Hz), 3.90 (s, 3H), 2.78 (s, 3H).

(S)-benzylmethylsulfoxide

Experiment Number 6

Colorless solid; 87% ee; DAICEL CHIRALCEL OB-H, hexane/isopropanol=80/20, flow rate=0.5 mL min$^{-1}$, $t_S$=22.9 min, $t_R$=29.5 min;
$^1$H NMR: δ 7.48-7.23 (m, 5H), 4.07 (d, 1H, J=12.9 Hz), 3.92 (d, 1H, J=12.7 Hz), 2.46 (s, 3H).

(S)-phenylethylsulfoxide

Experiment Number 7

Colorless oily substance; 81% ee; DAICEL CHIRALCEL OD-H, hexane/isopropanol=90/10, flow rate=0.5 mL min$^{-1}$, $t_R$=20.2 min, $t_S$=28.0 min;
$^1$H NMR: δ 7.66-7.58 (m, 2H), 7.57-7.47 (m, 3H), 2.96-2.85 (m, 1H), 2.82-2.71 (m, 1H), 1.20 (t, 3H, J=7.4 Hz).

Example 7

Dynamic Kinetic Resolution of Racemic Sulfoxide Using Iron-Salan Complex Catalyst

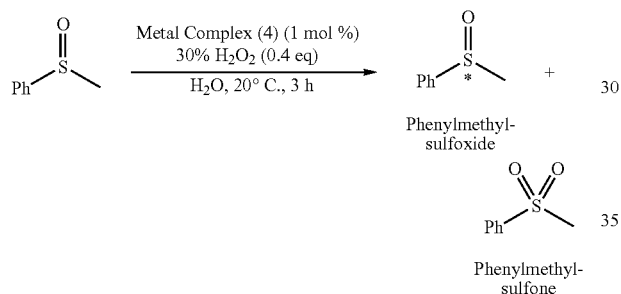

A complex (4) (1.9 mg, 1 mol %) was weighed out in a Schlenk flask, to which racemic phenylmethylsulfoxide (28 mg, 0.2 mmol) was added. Water (0.5 mL) was added, followed by stirring for 10 minutes at 20° C. A 30% hydrogen peroxide solution (9 μL, 0.4 eq) was added, followed by stirring the resultant mixture for 3 hours at room temperature. To the reaction mixture, water (5 mL) was added, followed by extraction using ethyl acetate. An organic phase was dried over anhydrous sodium sulfate, followed by filtration and then it was concentrated under reduced pressure. By purifying the concentrate using silica gel column chromatography (ethyl acetate), 6.5 mg (21% yield) of phenylmethylsulfone was obtained, and 22.1 mg of phenylmethylsulfoxide (79%) was recovered. Optical purity was determined to be 12% ee for a S form after measured by HPLC analysis.

The invention claimed is:

1. A process for producing an optically active sulfoxide compound comprising:

carrying out asymmetric oxidation, using an oxidizing agent, of a sulfide compound expressed by Formula (3):

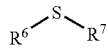

where $R^6$ and $R^7$ are different from each other and each of $R^6$ and $R^7$ is a $C_{6-12}$ aryl group that is not substituted or is substituted with a halogen atom, a $C_{1-4}$ alkyl group, a $C_{1-4}$ alkoxy group, a $C_{2-5}$ alkylcarbonyloxy group, a $C_{2-5}$ alkoxylcarbonyl group, a nitro group, or a cyano group;

a $C_{6-12}$ arylmethyl group that is not substituted or is substituted with a halogen atom, a $C_{1-4}$ alkyl group, a $C_{1-4}$ alkoxy group, a $C_{2-5}$ alkylcarbonyloxy group, a $C_{2-5}$ alkoxylcarbonyl group, a nitro group, or a cyano group;

a $C_{1-6}$ alkyl group that is not substituted or is substituted with a halogen atom, a nitro group, a hydroxyl group, or a cyano group; and when $R^6$ is a $C_{6-12}$ aryl group in which the ortho-position of the $C_{6-12}$ aryl group is substituted with a $C_{1-4}$ alkyl group or a $C_{1-4}$ alkoxy group, $R^7$ is optionally a $C_{2-4}$ bivalent group that forms a fused ring together with a sulfur atom binding to $R^6$, in the presence of an optically active metal complex expressed by Formula (1), Formula (1'), Formula (2), or Formula (2'):

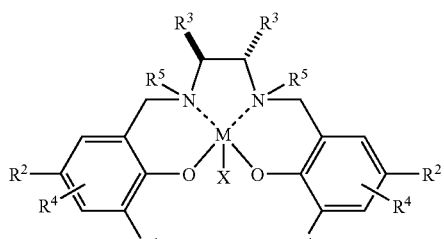

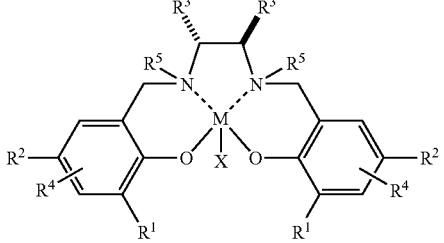

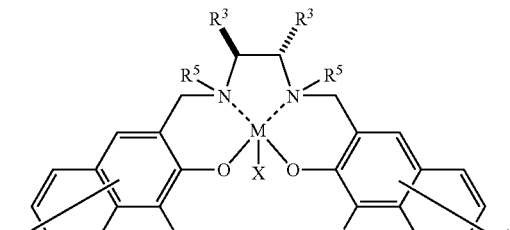

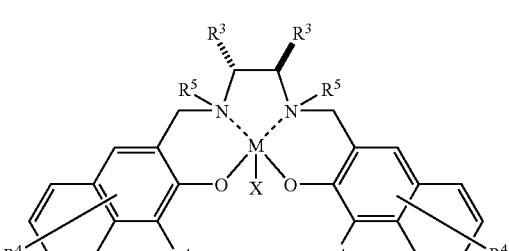

in Formula (1), Formula (1'), Formula (2), and Formula (2'), $R^1$ is
  a hydrogen atom,
  a halogen atom,
  a $C_{1-4}$ alkyl group,
  a $C_{1-4}$ alkoxy group,
  a $C_{6-12}$ aryloxy group, or
  a $C_{6-22}$ aryl group that is not substituted or is substituted with:
    a $C_{1-4}$ alkyl group, which is not substituted or is arbitrarily substituted with a halogen atom; or
    a $C_{1-4}$ alkoxy group, which is not substituted is not substituted with a $C_{6-12}$ aryl group, and
    when the $C_{6-22}$ aryl group forms an axial asymmetry with an aromatic ring in Formula (2) and Formula (2'), the axial asymmetry is optionally either optically active or optically inactive;
$R^2$ is a hydrogen atom, a halogen atom, a $C_{1-4}$ alkyl group, a $C_{1-4}$ alkoxy group, a $C_{6-12}$ aryloxy group, or a $C_{6-12}$ aryl group;
$R^3$ is a $C_{1-4}$ alkyl group, a $C_{6-18}$ aryl group, or a $C_{3-5}$ bivalent group in which two $R^3$s together form a ring;
$R^4$ is a hydrogen atom, a halogen atom, a $C_{1-4}$ alkyl group, a $C_{1-4}$ alkoxy group, a nitro group, or a cyan group independently;
$R^5$ is a hydrogen atom or a $C_{1-4}$ alkyl group;
M is an iron atom; and
X means an anion that is capable of forming an ion pair with M,
wherein the optically active sulfoxide compound is expressed by Formula (4):

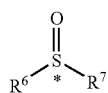

(4)

where $R^6$ and $R^7$ have the same meaning as defined in Formula (3) and an absolute configuration of a sulfur atom indicated with an asterisk (*) is R or S.

2. A process for producing an optically active sulfoxide compound comprising:
  converting, by selective oxidation using an oxidizing agent, a racemate or one of optical isomers of a sulfoxide compound with low optical purity expressed by Formula (5):

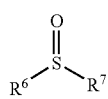

(5)

where $R^6$ and $R^7$ are different from each other and each of $R^6$ and $R^7$ is
  a $C_{6-12}$ aryl group that is not substituted or is substituted with a halogen atom a $C_{1-4}$ alkyl group, a $C_{1-4}$ alkoxy group, a $C_{2-5}$ alkylcarbonyloxy group, a $C_{2-5}$ alkoxylcarbonyl group, a nitro group, or a cyano group;
  a $C_{6-12}$ arylmethyl group that is not substituted or is substituted with a halogen atom, a $C_{1-4}$ alkyl group, a $C_{1-4}$ alkoxy group, a $C_{2-5}$ alkylcarbonyloxy group, a $C_{2-5}$ alkoxylcarbonyl group, a nitro group, or a cyano group;
  a $C_{1-6}$ alkyl group that is not substituted or is substituted with a halogen atom, a nitro group, a hydroxyl group, or a cyano group; or
  when $R^6$ is a $C_{6-12}$ aryl group in which the ortho-position of the $C_{6-12}$ aryl group is substituted with a $C_{1-4}$ alkyl group or a $C_{1-4}$ alkoxy group, $R^7$ is optionally a $C_{2-4}$ bivalent group that forms a fused ring together with a sulfur atom binding to $R^6$,
into a sulfone compound expressed by Formula (6):

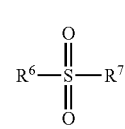

(6)

where $R^6$ and $R^7$ have the same meaning as defined in Formula (5),
in the presence of the optically active metal complex expressed by Formula (1), Formula (1'), Formula (2), or Formula (2'):

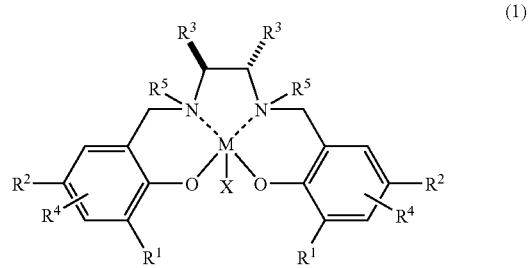

(1)

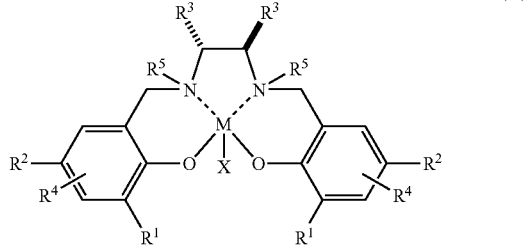

(1')

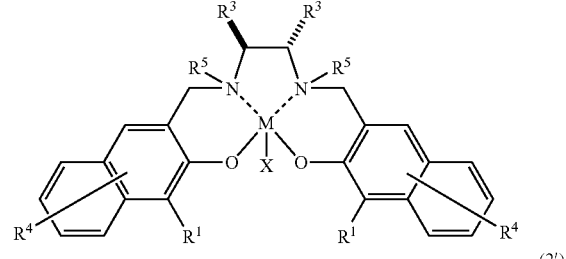

(2)

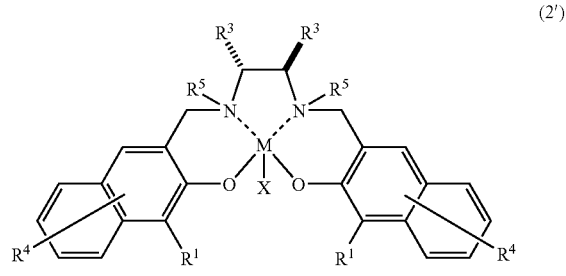

(2')

where $R^1$ is
a hydrogen atom,
a halogen atom,
a $C_{1-4}$ alkyl group,
a $C_{1-4}$ alkoxy group,
a $C_{6-12}$ aryloxy group, or
a $C_{6-22}$ aryl group that is not substituted or is substituted with:
  a $C_{1-4}$ alkyl group, which is not substituted or is arbitrarily substituted with a halogen atom; or
  a $C_{1-4}$ alkoxy group, which is not substituted or is substituted with a $C_{6-12}$ aryl group, and
  when the $C_{6-22}$ aryl group forms an axial asymmetry with an aromatic ring in Formula (2) and Formula (2'), the axial asymmetry is optionally either optically active or optically inactive;
$R^2$ is a hydrogen atom, a halogen atom, a $C_{1-4}$ alkyl group, a $C_{1-4}$ alkoxy group, a $C_{6-12}$ aryloxy group, or a $C_{6-12}$ aryl group;
$R^3$ is a $C_{1-4}$ alkyl group, a $C_{6-18}$ aryl group, or a $C_{3-5}$ bivalent group in which two $R^3$s together form a ring;
$R^4$ is a hydrogen atom, a halogen atom, a $C_{1-4}$ alkyl group, a $C_{1-4}$ alkoxy group, a nitro group, or a cyan group independently;
$R^5$ is a hydrogen atom or a $C_{1-4}$ alkyl group;
M is an iron atom; and
X means an anion that is capable of forming an ion pair with M,
to kinetically obtain an optically active sulfoxide compound expressed by Formula (4):

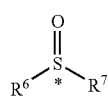

(4)

where $R^6$ and $R^7$ have the same meaning as defined in Formula (6) and an absolute configuration of a sulfur atom indicated as an asterisk (*) is R or S,
wherein water is used as a solvent.

3. The process for producing an optically active sulfoxide compound according to claim 1, wherein
when $R^6$ is a $C_{6-12}$ aryl group that is not substituted, or is substituted with:
a halogen atom;
a $C_{1-4}$ alkyl group;
a $C_{1-4}$ alkoxy group;
a $C_{2-5}$ alkylcarbonyloxy group;
a $C_{2-5}$ alkoxycarbonyl group;
a nitro group, or a cyano group; or
a $C_{6-12}$ arylmethyl group that is not substituted or is substituted with a halogen atom, a $C_{1-4}$ alkyl group, a $C_{1-4}$ alkoxy group, a $C_{2-5}$ alkylcarbonyloxy group, a $C_{2-5}$ alkoxycarbonyl group, a nitro group, or a cyano group,
$R^7$ is a $C_{1-4}$ alkyl group, or
when $R^6$ is a $C_{6-12}$ aryl group in which the ortho-position of the $C_{6-12}$ aryl group is substituted with a $C_{1-4}$ alkyl group or a $C_{1-4}$ alkoxy group, $R^7$ is a $C_{2-4}$ bivalent group that forms a fused ring together with a sulfur atom binding to $R^6$.

4. The process for producing an optically active sulfoxide compound according to claim 1, wherein hydrogen peroxide is used as an oxidizing agent.

5. The process for producing an optically active sulfoxide compound according to claim 1, wherein a reaction is carried out in the presence of an optically active metal complex,
in Formula (2) or Formula (2'),
  $R^1$ is a $C_{6-22}$ aryl group that is not substituted or substituted with a $C_{1-4}$ alkyl group, which is not substituted or arbitrarily is substituted with a halogen atom, or a $C_{1-4}$ alkoxy groups, which is not substituted or is substituted with a $C_{6-12}$ aryl group, and when the $C_{6-22}$ aryl group forms an axial asymmetry with an aromatic ring in Formula (2) or Formula (2'), the axial asymmetry is optionally optically active or optically Inactive;
  $R^3$ is a tetramethylene group in which two $R^3$s together form a ring;
  $R^4$ is a hydrogen atom;
  $R^5$ is a hydrogen atom or a methyl group; and
  X is a chlorine atom.

6. The process for producing an optically active sulfoxide compound according to claim 5, wherein the reaction is carried out in the presence of the optically active metal complex in which $R^1$ is an aryl group forming an axial asymmetry with an aromatic ring in Formula (2) or Formula (2') and the axial asymmetry is optically active.

7. The process for producing an optically active sulfoxide compound according to claim 6, wherein the reaction is carried out in the presence of the optically active metal complex in which $R^1$ is a 1-phenyl naphthyl group.

8. An optically active metal complex or an enantiomer thereof expressed by Formula (7):

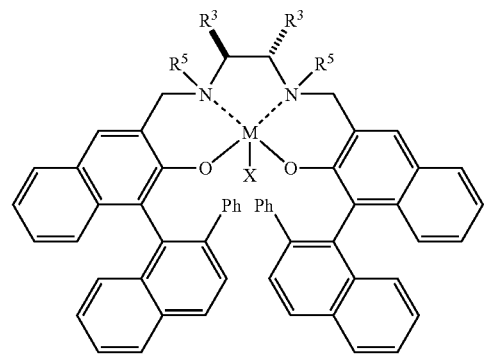

(7)

where
$R^3$ is a $C_{1-4}$ alkyl group, a $C_{6-18}$ aryl group, or a $C_{3-5}$ bivalent group in which two $R^3$s together form a ring;
$R^5$ is a hydrogen atom or a $C_{1-4}$ alkyl group;
M is an iron atom;
Ph is a phenyl group; and
X means an anion that is capable of forming an ion pair with M), in which a binaphthyl skeleton is optically active or optically inactive.

9. The process for producing an optically active sulfoxide compound according to claim 1, wherein water is used as a solvent.

* * * * *